US008617222B2

(12) United States Patent
Shipp et al.

(10) Patent No.: US 8,617,222 B2
(45) Date of Patent: Dec. 31, 2013

(54) NON-METALLIC ORTHOPEDIC PLATE (75) Inventors: Kenneth Shipp, Collierville, TN (US);
Ben Garden, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 908 days.

(21) Appl. No.: 11/668,292

(22) Filed: Jan. 29, 2007

(65) Prior Publication Data

US 2008/0033437 A1  Feb. 7, 2008

Related U.S. Application Data (63) Continuation of application No. 10/423,712, filed on Apr. 25, 2003, now Pat. No. 7,169,150.

(51) Int. Cl.
*A61B 17/80* (2006.01)

(52) U.S. Cl.
USPC ............................ 606/289; 606/290; 606/298

(58) Field of Classification Search
USPC ................................ 606/280–299, 300, 70–71
See application file for complete search history.

(56) References Cited

U.S. PATENT DOCUMENTS

| | | | | |
|---|---|---|---|---|
| 5,578,034 A * | 11/1996 | Estes | .............................. | 606/281 |
| 6,152,927 A * | 11/2000 | Farris et al. | .................... | 606/287 |
| 6,224,602 B1 * | 5/2001 | Hayes | ............................. | 606/296 |
| 6,273,889 B1 * | 8/2001 | Richelsoph | ....................... | 606/70 |
| 6,342,055 B1 * | 1/2002 | Eisermann et al. | ......... | 623/17.16 |
| 6,413,259 B1 * | 7/2002 | Lyons et al. | .................... | 606/295 |
| 6,454,769 B2 * | 9/2002 | Wagner et al. | ................. | 606/279 |
| 6,533,786 B1 * | 3/2003 | Needham et al. | ............. | 606/282 |
| 6,540,746 B1 * | 4/2003 | Buhler et al. | .................... | 606/60 |
| 6,652,525 B1 * | 11/2003 | Assaker et al. | ................ | 606/296 |
| 6,695,846 B2 * | 2/2004 | Richelsoph et al. | ............ | 606/71 |
| 6,755,833 B1 * | 6/2004 | Paul et al. | ......................... | 606/70 |
| 7,001,389 B1 * | 2/2006 | Navarro et al. | .................. | 606/71 |
| 7,025,769 B1 * | 4/2006 | Ferree | ............................ | 606/281 |
| 7,070,599 B2 * | 7/2006 | Paul | ................................ | 606/71 |
| 7,169,150 B2 * | 1/2007 | Shipp et al. | .................... | 606/287 |
| 2003/0078583 A1 * | 4/2003 | Biedermann et al. | ............ | 606/69 |
| 2004/0153069 A1 * | 8/2004 | Paul | ................................ | 606/61 |
| 2006/0079900 A1 * | 4/2006 | Mathieu et al. | .................. | 606/69 |
| 2006/0189982 A1 * | 8/2006 | Lange | ............................... | 606/61 |
| 2006/0241618 A1 * | 10/2006 | Gasser et al. | .................... | 606/72 |

FOREIGN PATENT DOCUMENTS

WO  200234159 A2  5/2002
WO  2004096068 A1  11/2004

* cited by examiner

*Primary Examiner* — Kevin T Truong
*Assistant Examiner* — Matthew Lawson (57) ABSTRACT A spinal plate comprises a body portion and at least one locking mechanism for engaging the body portion. The body portion is made of a radiolucent material, such as a polymer or polyether ether ketone (PEEK), and includes a plurality of bone screw openings for receiving a plurality of bone screws, such as bone screws. The at least one locking mechanism is for securing at least one of the plurality of bone screws when received into the body portion.

16 Claims, 4 Drawing Sheets

NON-METALLIC ORTHOPEDIC PLATE

CROSS REFERENCE

This application is a Continuation of, and claims the benefit of, U.S. patent application Ser. No. 10/423,712, entitled "Non-Metallic Orthopedic Plate" filed on Apr. 25, 2003, the entirety of which is incorporated by reference herein.

FIELD OF THE INVENTION

The present invention relates generally to bone plating systems, and more particularly, to a plating system for use in the treatment of various orthopedic pathologies.

BACKGROUND

The treatment of injuries to the spine has advanced significantly, including treatment for many forms of spinal injury and deformities that can occur due to disease, congenital effects, the effects of tumors, and, of course, fractures and dislocations attributable to physical trauma. For many years, the use of elongated rigid plates has been helpful in the stabilization and fixation of the spine.

It has been found that many plate designs allow for a uni-cortically or bi-cortically intrinsically stable implant. It has also been found that fixation plates can be useful in stabilizing the upper or lower cervical spine in traumatic, degenerative, tumorous or infectious processes. Moreover, these plates provide the additional benefit of allowing simultaneous neural decompression with immediate stability.

During the many years of development of cervical plating systems, particularly for the anterior approach, various needs for such a system have been recognized. For instance, the plate must provide strong mechanical fixation that can control movement of each vertebral motion segment in six degrees of freedom. The plate must also be able to withstand axial loading in continuity with each of the three columns of the spine. The plating system must be able to maintain stress levels below the endurance limits of the material, while at the same time exceeding the strength of the anatomic structures or vertebrae to which the plating system is engaged.

Another recognized requirement for a plating system is that the thickness of the plate must be small to lower its prominence, particularly in the smaller spaces of the cervical spine. The screws used to connect the plate to the vertebrae must not loosen over time or back out from the plate. Preferably the plate should be designed to contact the vertebrae for greater stability.

On the other hand, while the plate must satisfy certain mechanical requirements, it must also satisfy certain anatomic and surgical considerations. For example, the cervical plating system must minimize the intrusion into the patient and reduce the trauma to the surrounding soft tissue. It has also been found that optimum plating systems permit the placement of more than one screw in each of the instrumented vertebrae.

Many spinal plating systems have been developed in the last couple of decades that address some of the needs and requirements for cervical fixation systems. One example is the Anterior Cervical Plating System disclosed in U.S. Pat. No. 6,152,927, which is hereby incorporated by reference. However, even with the more refined plating system designs, there still remains a need for a spinal plating system that provides a high quality, durable device with modulus and mechanical strength properties similar to that of cortical bone. Metallic implants, with a substantially higher modulus than cortical bone, can cause a phenomenon known as "stress shielding," which is commonly thought to lead to bone mass loss and the loosening and subsequent failure of some metallic orthopedic implants. Additionally, radiographic qualities of metallic implants often produce imaging artifacts and scatter, which hinder the inspection of bone growth when using conventional imaging via X-ray, CAT scanning, or MRI techniques.

SUMMARY

In order to address the needs left unfulfilled by prior systems, the present invention provides a novel orthopedic plate. In one embodiment, a bone plate comprises a body portion and at least one locking mechanism for engaging the body portion. The body portion is made of a radiolucent material, such as a polymer or polyether ether ketone (PEEK), and includes a plurality of attachment mechanism openings for receiving a plurality of attachment mechanisms, such as bone screws. The at least one locking mechanism is for securing at least one of the plurality of attachment mechanisms when received into the body portion.

In some embodiments, the bone plate also includes at least one insert affixable with the body portion, the insert for engaging with the locking mechanism. The insert may comprise titanium, aluminum, or some other material that is different than the radiolucent material.

In some embodiments, the insert includes a rotation-prevention portion to thereby prevent rotation of the insert in the body portion. The insert may also include a metallic material for threadingly engaging with the locking mechanism. Also, the insert may be positioned along a longitudinal axis of the body portion to simultaneously engage with a plurality of locking mechanisms.

In another embodiment, a bone plate comprises a body formed primarily of a first material, wherein the body includes an opening for receiving an attachment mechanism, such as a bone screw. The bone plate also comprises an insert having one or more engaging portions, the insert including a second material different from the first material. The bone plate may also include a locking mechanism for engaging with the engaging portion. When engaged with the engaging portion, the locking mechanism secures the attachment mechanism in the corresponding opening.

In some embodiments, the first material is radiolucent, and the second material is radio-opaque. Also in some embodiments, the second material is harder than the first material.

In another embodiment, a spinal plating system is provided for promoting fusion between two or more vertebral bodies. The spinal plating system includes a plurality of attachment mechanisms, each of the attachment mechanisms having a centerline, and a body formed primarily of a non-metallic radiolucent material. The body includes an upper and a lower surface, and a plurality of attachment mechanism openings for receiving the plurality of attachment mechanisms. The spinal plating system also includes at least one threaded insert formed primarily of a metallic material, the insert being insertable into the at least one locking mechanism opening, wherein the threaded insert threadably receives the threaded locking mechanism, the threaded locking mechanism having a head that extends above the upper surface of the body. Each locking mechanism opening can be situated such that an attachment mechanism received in one of the attachment mechanism openings is lockably held by the threaded locking mechanism.

Many objects and benefits of the invention will become apparent upon consideration of the following written description of the invention, together with the accompanying Figures.

BRIEF DESCRIPTION OF THE DRAWINGS

FIG. 6b is a top perspective view of a threaded insert for use with the anterior cervical plating system of FIG. 6a.

DETAILED DESCRIPTION

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
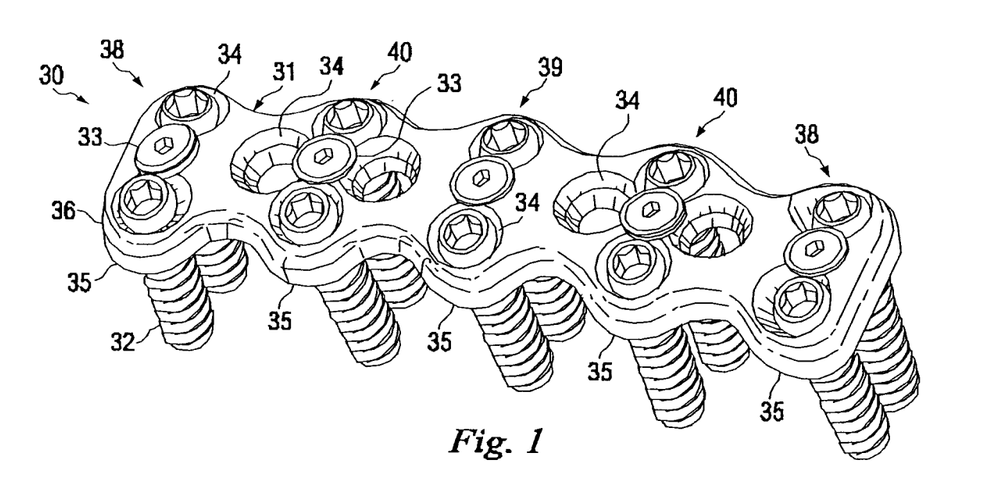
FIG. 1 is a top perspective view of an anterior plating system according to one embodiment of the present invention.
Figure 2:
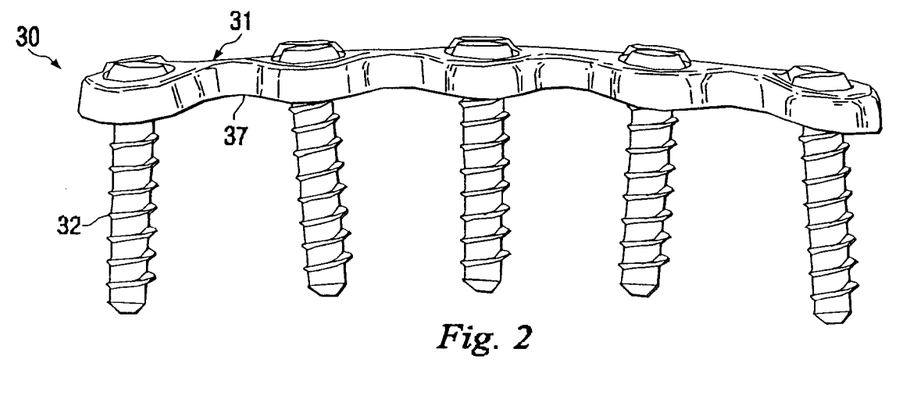
FIG. 2 is a side elevational view of the plating system shown in FIG. 1.

One embodiment of a bone plating system or fixation assembly 30 is depicted in FIGS. 1 and 2. In the present example, the bone plating system 30 is an anterior cervical plate, but it is understood that other plating systems can also benefit from the present invention. Other examples include plates or bone repair systems that can be used in the leg, the arm, the foot, the hand, or other parts of the body.

In accordance with the present embodiment, the plating system includes an elongated plate 31 and one or more bone attachment mechanisms 32, such as bone screws. Other bone attachment mechanisms include bolts, staples, and protrusions that can help to secure the plate in a desired position. The attachment mechanisms may be held or retained to the plate 31 by way of one or more locking assemblies 33. In the embodiments that use attachment mechanisms such as screws or bolts, the elongated plate 31 is provided with a plurality of openings or holes 34 in a variety of arrangements. The plate also can be divided into vertebral level nodes 35 with the attachment mechanisms 32 and openings 34 aligned at each node. Further, the plate 31 includes recesses between each of the nodes 35 to reduce the outer contour and size of the plate. In addition, the reduced width portion between each of the nodes 35 provides an area of reduced material for additional bending of the plate as may be required by the spinal anatomy.

The plate 31 is constructed, primarily, of a radiolucent material, such as a polymer based resin. In one embodiment, the plate 31 is constructed substantially from a polyether ether ketone (PEEK) high temperature thermoplastic commercially available by Invibio Biomaterial Solutions of Lancashire, UK under the tradename PEEK-OPTIMA. Using such material, conventional imaging of bony structures associated with the plate 31, such as with X-ray, computerized axial tomography (CAT) scanning, or magnetic resonance imaging (MRI) is improved due to the lack of imaging artifacts and scatter compared to that generated from metallic implants. Also, polymers such as PEEK will bow and bend to a limited degree. This flexibility can be used to provide better healing/fusion between the fractured bone or fused vertebral bodies by allowing increased relative motion and avoiding stress shielding.

The plate 31 can further include one or more bone growth or fusion-promoting elements, such as bone, bone morphogenetic protein (BMP), demineralized bone matrix (DBM), LIM mineralization proteins (LMP), osteogenic pastes, and so forth. It is understood that such fusion-promoting elements are well known by those of ordinary skill in the art.

The plate 31 can include a rounded upper edge 36 to reduce irritation of surrounding tissue, for example, in a spinal fusion procedure, the rounded upper edge would be in contact with the soft tissue surrounding the spine. The rounded upper edge 36 reduces the amount of trauma or irritation that would be experienced by the surrounding soft tissue. The bottom surface 37 of the plate 31 is preferably configured to contact and engage the fractured bone or vertebral bodies at each of the instrumented levels of the spine. In some embodiments, the bottom surface can be textured to enhance its grip on the vertebral body and may have a longitudinal and/or transverse curvature to match the corresponding attachment surface (e.g., the curve of the spine).

Figure 3A:
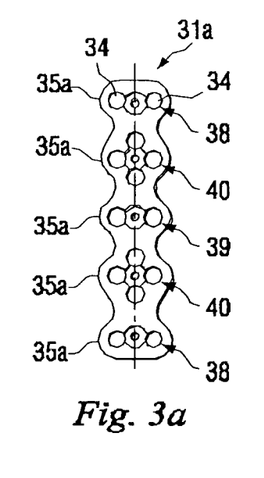
FIGS. 3a-3g are top elevational views of a fixation plate in accordance with different embodiments of the present invention, provided in different sizes and configuration.
Figure 3B:
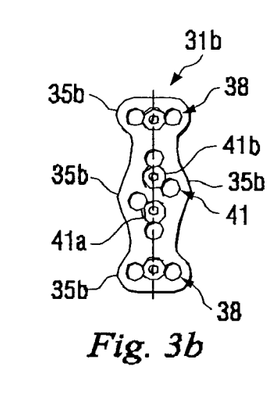

Referring now to FIGS. 3a-3g, several variations of the elongated plate 31 are depicted. It is understood that the bone plating system according to the present embodiment can be readily adapted to fix several fractured bony pieces or vertebrae, of course depending upon the size/length of the plate and the number and arrangement of attachment mechanisms. For example, the plate depicted in FIGS. 1, 2 and 3a includes five vertebral level nodes 35a so that the plate can be engaged to five vertebrae of the spine. The plate 31a of FIG. 3a could be used to fix the vertebrae C2-C6, although the plate also may be used in thoracic, lumbar, and sacral regions of the spine. The elongated plates 31b depicted in FIG. 3b is sized and configured to span three vertebrae, depending upon the instrumented vertebral levels. In this instance, the plate 31b includes three vertebral level nodes 35b, with two nodes at the opposite ends of the plate and one node with attachment mechanisms offset from each other in the middle portion of the plate to accommodate variation in vertebral anatomy.

Figure 3C:
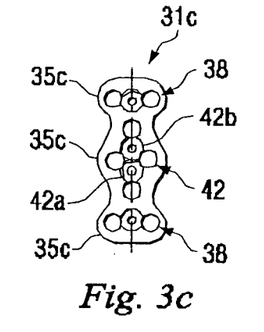

A modification of the plate 31b is depicted in FIG. 3c. In this case, the plate 31c includes three nodes 35c, with the nodes on the opposite side of the middle portion of the plate being directly aligned at the same vertebral level. The plates of FIGS. 3d-3e, namely plates 31d and 31e, are similar to the plate 31c although their lengths are progressively shorter to accommodate varying vertebral body height. The last two plates 31*f* and 31*g*, in FIGS. 3*f*-3*g*, respectively, provide for instrumentation of two vertebral levels, each having two nodes 35*f* and 35*g*, respectively.

The elongated plates 31*a*-31*g* can provide a variety of hole patterns at each of the nodes 35*a*-35*g*. These hole patterns can provide for at least two attachment mechanisms (e.g., screws) to be engaged into each respective bony portion (e.g., vertebral body). As discussed above, it has been found that the placement of two or more screws in each vertebral body improves the stability of the construct.

The present embodiments may also provide a mechanism for locking the attachment mechanisms to the elongated plate to prevent backout, loosening, or other dis-engagement of the attachment mechanisms. Consequently, in a further aspect of the embodiments, various openings hole patterns may be provided. One pattern is an end hole pattern 38, as shown at the ends of plate 31 in FIG. 1 and plate 31*a* in FIG. 3*a*. In this arrangement, two screw holes 34 are laterally disposed at a single node 35*a*. A single locking assembly may be disposed between the two screw holes 34 and configured to lock attachment mechanisms disposed within the plate 31*a*. The locking assembly can be a machine screw that engages with threads in the plate 31*a*, or can be a self-tapping screw that cuts through the plate as it is advanced therein. Other types of locking assemblies include a rotatable disk, lever, or rivet shaped to selectively allow one or more attachment mechanisms to be inserted and locked; a deformable portion (e.g., a washer) that selectively allow one or more attachment mechanisms to be inserted and locked; strap/tie mechanisms that can be used to selectively tie down one or more attachment mechanisms; and a sliding member for moving between different positions to selectively allow one or more attachment mechanisms to be inserted and locked. A similar arrangement can be provided by the middle hole pattern 39 in which two screw holes are situated at a single vertebral level. A locking assembly can be disposed between the two attachment mechanism holes and configured to lock the respective attachment mechanisms.

Figure 3D:
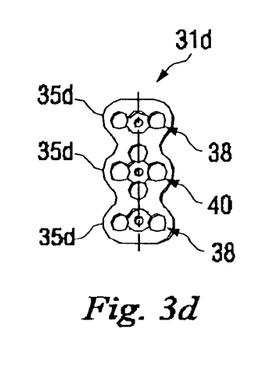
Figure 3E:
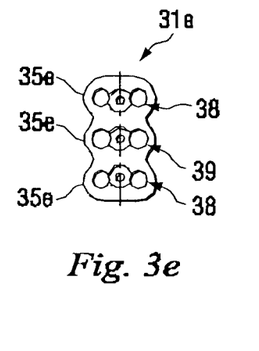

The present embodiment further contemplates a plate carrying four-attachment mechanism patterns. For the sake of example, the four-hole pattern 40 illustrated in FIG. 1 and FIGS. 3*a* and 3*d*, provides for four bone screws holes in a diamond pattern. A single locking assembly 33 can be centrally disposed between all of the attachment mechanism holes so that attachment mechanisms within the respective holes are simultaneously locked by the single locking assembly. In the five node plate 31*a* of FIG. 3*a*, two such four-hole patterns 40 are provided. In the three-node plate 31*d* of FIG. 3*d*, only a single four-hole pattern 40 is required. It can be appreciated that the four-hole pattern 40 provides a great degree of flexibility to the surgeon in determining how many attachment mechanisms 32 will be engaged into a single vertebra, and in what arrangement. For example, as shown in FIG. 1, two screws are situated in the laterally opposite screw holes at the vertebral level node 35. Alternatively, attachment mechanisms could be placed in the longitudinally opposite screw holes oriented along the length of the plate 31*a*. Other arrangements contemplate attachment mechanisms being placed in immediately adjacent screw holes 34, or placing three attachment mechanisms in three of the holes of the four-hole pattern 40. Again, the selection of attachment mechanisms and their arrangement can be left to the surgeon and will be based upon the type of correction or fixation required and the anatomy of bony member being addressed.

A further arrangement for attachment mechanisms is provided by the four-hole cluster 41 depicted in FIGS. 3*b* and 3*c*. In the four-hole cluster 41 in plate 31*b*, two hole pairs 41*a* and 41*b* are provided. Each of the hole pairs may include its own locking assembly to lock the two attachment mechanisms (e.g., screws) into the screw bores of the respective hole pairs. As shown in FIG. 3*b*, the orientation of the particular hole pairs provides one screw hole from each pair generally laterally relative to each other in a single bony portion (e.g., vertebra). The other of the attachment mechanism holes in each respective pair is longitudinally offset from the central screw holes, being disposed closer to the ends of the plate 31*b*. In this manner, the two central holes of each of the two holes pairs can be engaged in a single vertebra, while the remaining screw holes of the hole pairs 41*a* and 41*b* can be disposed in the superior and inferior adjacent vertebrae. Most preferably, however, each of the screw holes in the four-hole cluster 41 is generally oriented over or slightly offset from a single vertebra. The surgeon then has the option to selected any of the screw holes in the two hole pairs 41*a* or 41*b* that is optimally aligned over the vertebra.

A similar arrangement is found in the plate 31C which includes a four-hole cluster 42. In this example, it can be seen that the four-hole cluster 42 includes two hole pairs 42*a* and 42*b*, in a manner similar to the four-hole cluster 41 of FIG. 3*b*; however in this case, the hole pairs are arranged closer to each other, principally because the plate 31*c* is shorter than the plate 31*b*. In both of the four-hole clusters 40 and 41, the locking assemblies are provided to lock only a pair of attachment mechanism holes rather than all four holes with a single locking assembly.

Figure 3F:
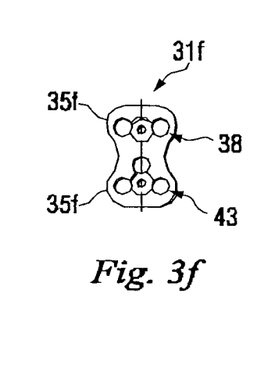
Figure 3G:
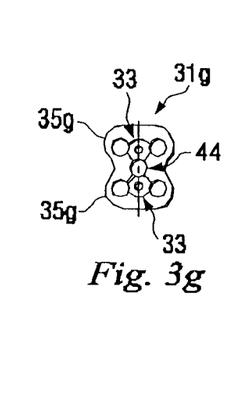

The invention further contemplates a three-hole pattern, such as pattern 43 provided in the plate 3 if in FIG. 3*f*. In this example, a single locking assembly is used to fix three attachment mechanisms within the respective screw holes. A five-hole pattern 44 is provided on plate 31*g*, as shown in FIG. 3*g*. In this example, a single hole is arranged centrally between four outlying holes. Two locking assemblies 33 are provided to lock a pair of the outlying four screw holes together with the central hole. In this configuration, the central hole is held in place by two locking assemblies, while each of the outlying pair of holes is held in place by a single locking assembly.

Figure 4:
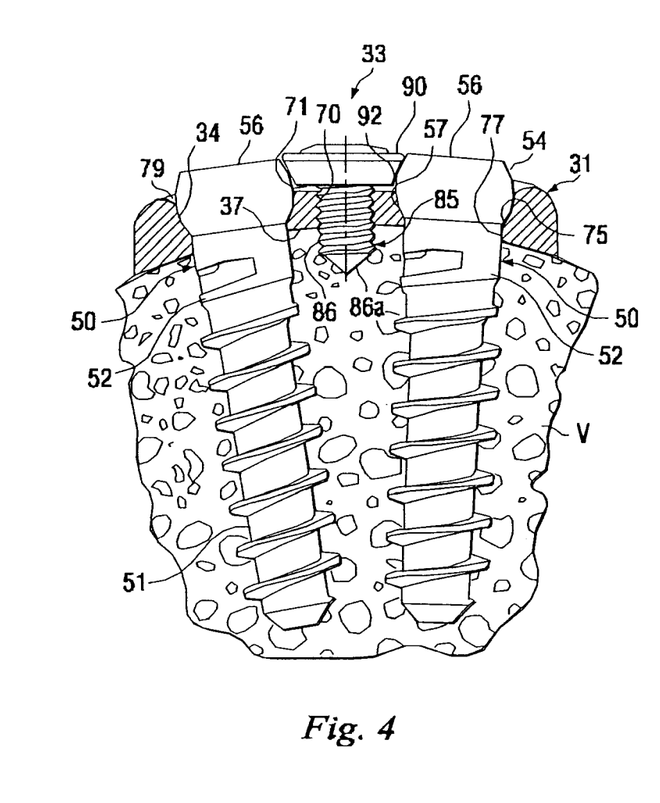
FIG. 4 is a partial cross-sectional view of a plate according to an embodiment of the present invention with the fixed angle attachment mechanisms disposed within bone holes in a plate and engaged within a vertebra.
Figure 5:
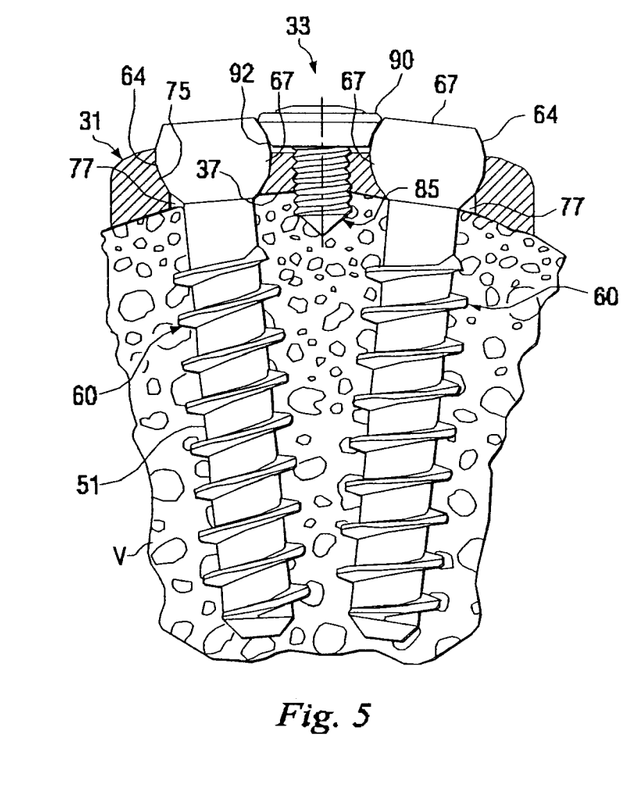
FIG. 5 is an enlarged end cross-sectional view of the plate according to an embodiment of the present invention with variable angle screws disposed in the plate and engaged in a vertebra.

Referring now to FIGS. 4 and 5, the use of the fixation plate assembly 30 is illustrated using, for the sake of example, bone screws for affixing to a vertebral body V. In FIG. 4, a pair of fixed angle screws 50 are disposed within respective bores 34 so that the threaded shanks 51 project beyond the lower surface 37 of the plate 31 and into the vertebral body V. The threaded shank is preferably configured to engage the cortical and cancellous bone of the vertebral body V. The intermediate portion 52 of the fixed angle screw 50 extends through the cylindrical bore 77 of the screw holes 34. The spherical surface 57 of the head 54 of the screw contacts the spherical recess 75 of the screw hole 34 as the fixed angle screw 50 is threaded into the vertebral body V. Once the screw 50 is completely seated within the spherical recess 75, the intermediate portion 52 provides a snug relationship relative to the cylindrical bore 77 so that the fixed angle screw 50 is not able to pivot or translate relative to the plate 31.

In order to ensure secure fixation of the screw 50 within plate 31, the locking assembly 33 is tightened onto the heads 54 of the two attachment mechanisms 50. In particular, a locking mechanism 85, such as a locking screw, is threaded into the bore 70 to draw the washer 90 into contact with the screw heads. In the present embodiment, the bore 70 is already tapped, although in other embodiments the locking mechanism 85 may be a self tapping screw. Further embodiments of the locking mechanism 85 include a disk, lever, rivet, or other mechanical structure configured or shaped to selectively allow one or more attachment mechanisms to be inserted and/or locked; a deformable portion (e.g., a washer)

that selectively allow one or more attachment mechanisms to be inserted and/or locked; strap/tie mechanisms that can be used to selectively tie down one or more attachment mechanisms; and a sliding member for moving between different positions to selectively allow one or more attachment mechanisms to be inserted and/or locked.

The convex surface 92 seats against the spherical surface 57 of the attachment mechanism heads 54 to firmly seat the screw heads within the plate spherical recess 75. In some embodiments, the locking washer 90 can advance sufficiently far into the locking recess 71 to rest substantially flush with the top surfaces 56 of the attachment mechanisms 50.

In a further aspect of the present embodiments, the locking assembly 33 can be loosely fixed on the plate 31 so that the surgeon does not have to attach the locking assembly when the plate is engaged to a vertebra or other bony member. In the present example, the locking mechanism 85 is a screw that is pre-threaded through the locking washer 90 and into the tapped bore 70 until about three or fewer threads of the locking screw project below the bottom surface 37 of the plate. The locking screw 85 is then staked at the thread furthest from the plate so that the screw cannot be removed or backed out through the tapped bore 70. Of course, the locking screw 85 can be advanced further through the bore 70—when it is necessary to enable the locking assembly 33. As previously mentioned, the sharp point 86a of the locking screw 85 is preferably configured to penetrate the cortical bone. With the locking screw staked to the plate, the sharp point 86a will penetrate the vertebra V when the plate 31 is initially positioned on the bone. In this instance, the locking screw 85 helps locate and temporarily stabilize the plate on the vertebra V as the attachment mechanisms 50 are implanted into the bone. This temporary location feature provided by the locking screw 85 can also be used when a drill guide is used to drill and tap the vertebra to receive the attachment mechanisms 50.

The locking assembly 33 can be configured so that the washer 90 can be moved clear of the screw holes 34 when the locking screw 85 is staked to the plate 31. Thus, even with the locking assembly 33 in its loosened position, the attachment mechanisms 50, 60 can still be inserted into the screw holes 34.

The use of the variable angle attachment mechanism 60 is depicted in FIG. 5. The locking assembly 33 functions as described above to lock the heads 64 of the variable angle screws 60 within the plate 31. Specifically, the convex surface 92 of the washer 90 contacts and applies pressure to the spherical surfaces 67 of the respective attachment mechanisms 60. However, with the variable angle screws 60, the intermediate portion 62 does not fit snugly within the cylindrical bore 77 of the screw holes 34. Thus, even with the head 64 of each screw 60 residing solidly within the spherical recess 75, the attachment mechanism 60 can still be angulated relative to the plate and to the axis of the spherical recess 75 and cylindrical bore 77. It is understood that the degree of angulation is restricted by the difference in diameters between the cylindrical bore 77 and the intermediate portion 62 of the variable angle screw 60. In one preferred embodiment, the relative diameters permit angulation of up to 20° from the axis 75a of the recess 75 and bore 77.

During implantation, the variable angle capability of the screw 60 allows the surgeon to place the attachment mechanism within the vertebra at any angle within the defined angulation limits (20° in one specific embodiment). Thus, the variable angle screw 60 provides greater flexibility than does the fixed angle screw 50 for orienting the attachment mechanism relative to the anatomy of the vertebra. Moreover, this variable angle capability allows a limited degree of micromotion between the screw and the plate when the fixation assembly 30 is implanted within a patient. In other words, as the spine is loaded and as load is transmitted through the screws and plate, the plate and vertebra may translate relative to each other. The variable angle screw 60 accommodates this relative movement by pivoting within the spherical recess 75. On the other hand, the fixed angle screw 50 prevents this relative movement. The choice between using a fixed or a variable angle screw can be left to the surgeon depending upon the pathology being treated. The fixation plate assembly 30 according to the present embodiment allows this choice to be made at any point during the surgical procedure.

The plating system 30 of FIGS. 1-5 include many benefits. By using a non-metallic substance such as PEEK, the plate 31 obtains a degree of flexibility, when compared to metallic plates, while still providing a strong mechanical fixation that can control movement of each vertebral motion segment in six degrees of freedom. The plating system 30 is also be able to withstand axial loading in continuity with each of the three columns of the spine. The plating system 30 is able to maintain stress levels below the endurance limits of the PEEK material, while at the same time exceeding the strength of the anatomic structures or vertebrae to which the plating system is engaged. The thickness of the plate 31 is relatively small, thereby lowering its prominence, particularly in the smaller spaces of the cervical spine. The PEEK material allows locking screws to be self-tapped, as contrasted with metallic plates. And, the flexible properties of the PEEK material help to prevent attachment mechanisms from loosening or backing out from the plate 31 and the vertebral bodies.

Figure 6A:
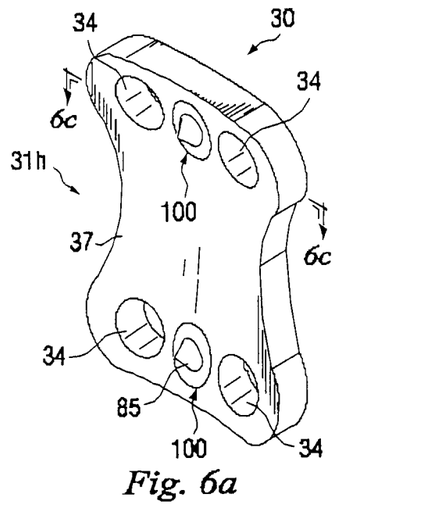
FIG. 6a is a bottom perspective view of an anterior plating system according to another embodiment of the present invention.
Figure 6B:
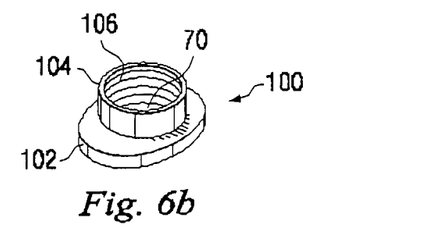
Figure 6C:
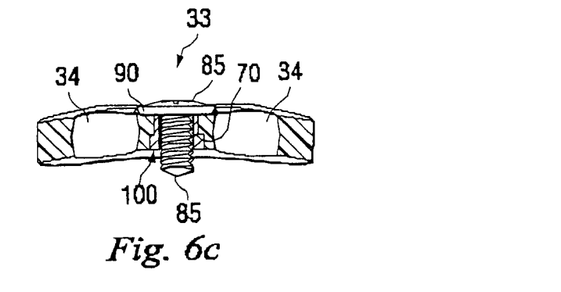
FIG. 6c is a side cross-sectional view of the plate shown in FIG. 6a taken along line 6c-6c as viewed in the direction of the arrows.

Referring now to FIGS. 6a-6c, in another embodiment of the plating system 30, plate 31h is similar to plate 3 if (FIG. 3f) with the inclusion of a metallic insert 100. In the present embodiment, the metallic insert is made of titanium aluminum, or ceramic, although other materials can also be used. The metallic insert 100 is used for part of the locking assembly 33 to provide an improved interface for receiving and securing the locking screw 85.

Referring specifically to FIG. 6b, the metallic insert 100 includes an oval shaped portion 102 and a cylindrical portion 104. The cylindrical portion 104 includes a threaded interior wall 106 for receiving and threadingly engaging with the locking mechanism 85. Referring to FIGS. 6a and 6c, in one embodiment, the metallic insert 100 is pressed into the plate 31h, preferably when the plate is in a more malleable state.

The plating system 30 of FIGS. 6a-6c include many benefits. In addition to the benefits listed above with reference to FIGS. 1-5, the metallic inserts 100 provide extra strength for the locking assemblies 33. Also, the metallic inserts 100 are easily threaded, so that the locking mechanism 85 can be of a very tight manufacture (e.g., a tightly threaded screw as compared to a self-tapping screw). The oval shaped portion 102 prevents any rotation of the insert 100 when the locking mechanism 85 is being inserted into or removed from the plating system 30. Also, the oval shaped portion 102 prevents the insert from being removed in a direction opposite to the bottom surface 37 of the plate 31.

Figure 7A:
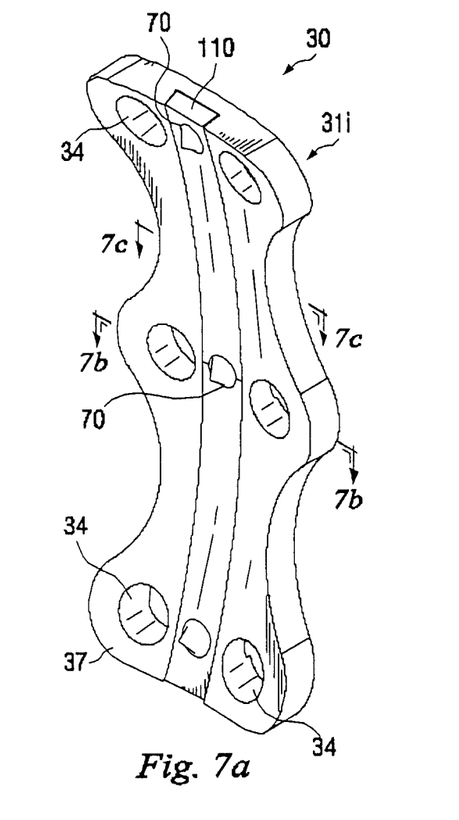
FIG. 7a is a bottom perspective view of an anterior plating system according to another embodiment of the present invention.
Figure 7B:
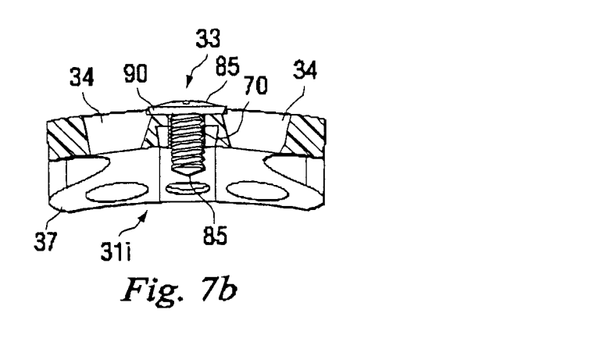
FIGS. 7b and 7c are side cross-sectional views of the plate shown in FIG. 7a taken along line 7b-7b and 7c-7c, respectively, as viewed in the direction of the arrows.
Figure 7C:
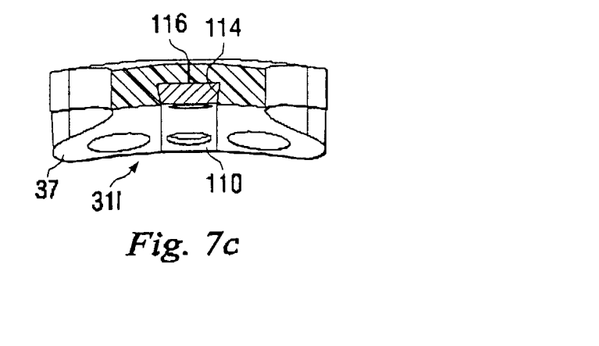

Referring now to FIGS. 7a-7c, in another embodiment of the plating system 30, plate 31i is similar to plate 31e (FIG. 3e) with the inclusion of a metallic insert 110. In the present embodiment, the metallic insert is made of titanium or aluminum, although other materials can also be used. The metallic insert 110 extends along a longitudinal axis of the plate 31i, thereby stiffening and strengthening the plate and reducing an amount of bow that would otherwise occur. The metallic insert 110 also provides anti-compression strength along its longitudinal axis. In some embodiments, the metallic insert 110 provides one or more threaded interior walls 112 for receiving and threadingly engaging with screw-type locking mechanisms 85. The extended shape of the metallic insert 110 prevents any rotation of the insert 100 when the locking mechanism 85 is being inserted into or removed from the plating system 30. Although the metallic insert 110 is illustrated as a single unit, it may be comprised of multiple units.

In one embodiment, the metallic insert 110 is formed as a dove tail, with an upper surface (as shown in FIG. 7c) that is larger than its lower surface. The dove tail shape of the metallic insert fits like a "key" into a corresponding slot 114 of the plate 31i. In the present embodiment, the dove tail shape also allows the insert 110 to be slid into the plate 31i, so that one or more of the threaded portions of the insert are aligned with one or more of the bores 70. In some embodiments, a pin 116 may also (or alternatively) be used to secure the metallic insert 110 into the plate. It is known that there are many different ways to secure the metallic insert 110 to the plate 31i, and the locking screws 85 themselves can be the sole source of securement.

The plating system 30 of FIGS. 7a-7c include many benefits. In addition to the benefits listed above with reference to FIGS. 1-6c, the metallic inserts 110 provide extra strength for several different locking screws 85. A single metallic insert 110 can easily be slid into the plate 31i, thereby making manufacturing easier. Alternatively, several metallic plates (e.g., one for each locking screw 85) can be sequentially slid into the slot 114 of the plate 31i, thereby having a reduced number of insert sizes accommodating the different potential shapes and lengths (e.g., FIGS. 3a-3g) that may be used for the plate 31i.

Although only a few exemplary embodiments of this invention have been described in detail above, those skilled in the art will readily appreciate that many modifications are possible in the exemplary embodiments without materially departing from the novel teachings and advantages of this invention. For example, one or more visualization windows (apertures) can be made in the plate 31 to facilitate the visual placement of the plating system by a surgeon. Also, features illustrated and discussed above with respect to some embodiments can be combined with features illustrated and discussed above with respect to other embodiments. Accordingly, all such modifications are intended to be included within the scope of this invention.

We claim:

1. A bone plate system comprising:
a body portion having a length comprising:
a plurality of attachment-mechanism openings for receiving a plurality of attachment mechanisms configured for engaging bone;
at least one locking-member opening adjacent to at least two of the plurality of attachment-mechanism openings, the at least one locking-member opening sized and shaped to receive a locking member configured to secure at least two of the plurality of attachment mechanisms to the body portion;
a bone-engaging surface for positioning adjacent to a bone;
a slot extending along a majority of the length of the body portion for receiving an insert, the slot comprising a recess in the bone-engaging surface;
an insert for positioning within the slot of the body portion, the insert having at least one opening extending therethrough, the at least one opening positioned such that when the insert is received within the slot the at least one opening is aligned with the at least one locking-member opening; and
at least one locking member for engaging with the at least one locking-member opening of the body portion, the at least one locking member sized and shaped such that when the locking member is engaged with the locking-member opening a portion of the locking member extends into the at least one opening of the insert and fixedly secures to the body portion at least two of the plurality of attachment mechanisms received within the at least two of the plurality of attachment-mechanism openings that are adjacent to the at least one locking-member opening.

2. The bone plate system of claim 1, wherein the slot is dovetailed.

3. The bone plate system of claim 1, wherein the bone-engaging surface is concave.

4. The bone plate system of claim 1, wherein the plurality of attachment-mechanism openings are spaced along the length of the body portion.

5. The bone plate system of claim 4, wherein the body portion has a first width adjacent to the plurality of attachment-mechanism openings and a second width in the space between the plurality of attachment-mechanism openings, the first width being greater than the second width.

6. The bone plate system of claim 4, wherein the plurality of attachment-mechanism openings are equally spaced along the length of the body portion.

7. The bone plate system of claim 4, wherein the at least one locking-member opening is positioned between a pair of attachment-mechanism openings.

8. The bone plate system of claim 1, wherein the body portion comprises a radiolucent material.

9. The bone plate system of claim 8, wherein the body portion comprises PEEK.

10. A bone plate assembly comprising:
a plurality of attachment mechanisms for engaging with a bone;
a body portion including a polymer material and comprising:
a plurality of attachment-mechanism openings for receiving the plurality of attachment mechanisms, and
at least one locking-member opening adjacent to each of the plurality of attachment-mechanism openings, the at least one locking-member opening having a portion with an oval profile;
at least one insert having a portion with an oval profile for engaging with the oval portion of the at least one locking-member opening of the body portion, the insert having a threaded cylindrical opening extending therethrough for receiving a locking mechanism; and
at least one locking-mechanism for threadingly engaging the at least one insert to fixedly secure the body portion to the plurality of attachment mechanisms.

11. The bone plate assembly of claim 10, wherein the at least one locking mechanism is configured to engage the bone.

12. The bone plate assembly of claim 10, wherein the oval shaped portion of the insert prevents rotation of the insert relative to the body as the locking mechanism is threadingly engaged with the insert.

13. The bone plate assembly of claim 10, wherein the at least one locking mechanism comprises a screw.

14. The bone plate assembly of claim 13, wherein the screw is threadable to at least partially engage a bone.

15. The bone plate assembly of claim 10, wherein the at least one insert portion comprises a radiopaque material.

16. The bone plate assembly of claim 15, wherein the radiopaque material comprises a metal.

* * * * *